United States Patent [19]

McClelland et al.

[11] Patent Number: 4,946,686
[45] Date of Patent: Aug. 7, 1990

[54] SOLUBILITY MODULATED DRUG DELIVERY SYSTEM

[75] Inventors: Gregory A. McClelland, Lenexa; Gaylen M. Zentner, Lawrence, both of Kans.

[73] Assignee: Merck & Co., Inc., Rahway, N.J.

[21] Appl. No.: 348,099

[22] Filed: May 1, 1989

Related U.S. Application Data

[63] Continuation-in-part of Ser. No. 100,664, Sep. 24, 1987, abandoned.

[51] Int. Cl.$^5$ ............................................. A61K 9/22
[52] U.S. Cl. ................................. 424/473; 424/482
[58] Field of Search ........................ 424/469, 473, 482

[56] References Cited

U.S. PATENT DOCUMENTS

| | | | |
|---|---|---|---|
| 4,693,895 | 9/1987 | Wong et al. | 424/469 |
| 4,795,644 | 1/1989 | Zentner | 424/468 |
| 4,814,183 | 3/1989 | Zentner | 424/443 |

Primary Examiner—Olik Chaudhuri
Assistant Examiner—Andrew Griffis
Attorney, Agent, or Firm—Kevin J. McGough; Michael C. Sudol, Jr.; Joseph F. DiPrima

[57] ABSTRACT

A drug delivery device for the controlled release of a therapeutically active ingredient into an environment of use is disclosed which comprises:
(A) a core composition comprising
  (a) a plurality of controlled release solubility modulating units comprising solubility modulating agents each of which is a complexing agent or a surfactant and which is either (i) surround by a water insoluble cost containing at least one pore forming additive dispersed throughout said coat, or (ii) dispersed in an individual matrix substrate, and
  (b) A therapeutically active ingredient; and
(B) a water insoluble microporous wall surrounding said core composition comprising:
  (i) a polymer material that is permeable to water but substantially impermeable to solute and
  (ii) 0.1 to 75% by weight, based on the total weight of (i) and (ii), of at least one water leachable pore forming additive dispersed throughout said wall.

8 Claims, 2 Drawing Sheets

SOLUBILITY MODULATED DRUG DELIVERY SYSTEM

This application is a continuation of U.S. Pat. Application Ser. No. 100,664, filed Sep. 24, 1987, which is now abandoned.

FIELD OF THE INVENTION

This invention pertains to both a useful and novel drug-delivery device for dispensing a drug to an environment of use. Particularly, the invention pertains to an osmotic drug delivery device containing a controlled release drug solubility modulator that regulates the solubility of the drug(s) within the device. This regulation affects the release profile of the drug from the device. Consequently, selecting the proper drug solubility modulator allows the release of drug to be controlled by the delivery device and not by the intrinsic water solubility of the drug or the environment surrounding the device. In the instant invention solubility modulation of drugs is achieved through use of solubility modulating complexing agents and surfactants.

BACKGROUND OF THE INVENTION

The need for systems that can deliver a drug at a controlled rate of release to an environment of use over a specified period of time is well established.

Devices for the controlled and continuous delivery of an active agent made from microporous materials are known to the prior art. Generally, the agent is embedded in or surrounded by the material and its release therefrom often is adversely influenced by external conditions. For example, U.S. Pat. No. 2,846,057 discloses a device consisting of a porous cellophane wall surrounding sodium fluoride that is released by water flowing into the pores to dissolve and leach it from the device. Controlled release is hard to obtain with this device because release is governed by external conditions and not by the device. That is, the amount of fluoride released changes with the rate of flow of water, with higher rates increasing the amount released, and lower rates decreasing the amount released over time. Similarly, U.S. Pat. No. 3,538,214 discloses a device consisting of drug coated with a film of water insoluble plastic containing a modifying agent that is soluble at a certain pH. When this device is in the gastro-intestinal tract, the modifying agent is partially or fully dissolved from the film by gastro-intestinal fluid to form a porous film. This lets fluid through the film to dissolve the drug and leach it outwards through the pores into the tract. Controlled release is difficult to achieve with this device because the selection of the modifying agent is based on the unknown acid and alkaline state of the gastro-intestinal tract which concomitantly influences pore formation and the exposure of drug to fluid. A similar device is disclosed in U.S. Pat. No. 2,928,770. The device of this patent consists of an outer layer of drug coated onto a porous material having its pores filled with a softened wax that is supposedly removed in the gastrointestinal tract by the alimentary fluid. This device cannot be relied on for controlled release because it too requires in situ pore formation which is dominated by unregulated external conditions and not by the device. The use of pore formers in substantially water impermeable polymers is disclosed in *J. Pharm. Sci.* 72, p. 772–775 and U.S. Pat. Nos. 4,557,925; 4,244,941; 4,217,898; 3,993,072. These devices release the core components by simple diffusion only and would be subject to environmental agitation.

U.S. Pat. No. 3,957,523 discloses a device which has a pH sensitive pore former in the device wall. U.S. Pat. Nos. 4,309,996; 4,320,759; 4,235,236 disclose devices with a microporous coat containing a swelling polymer as the driving force for delivery of agents. U.S. Pat. Nos. 4,256,108; 4,160,452; 4,200,098 and 4,285,987 disclose devices with pore formers in only one of multiple wall layers. These devices contain a drilled hole through a semipermeable coating which is impermeable to dissolved drugs and solutes. U.S. Pat. No. 4,326,525 is also based on semipermeable membrane technology with a drilled hole acting as exit portal for the drug. This patent discloses the use of buffers which react via proton-transfer or neutralizing reactions with the drug to produce a new drug agent which has different thermodynamic properties from the parent drug.

U.S. Pat. No. 4,755,180 to Ayer describes solubility modulation through use of a plurality of units comprising buffers and osmagents. These buffers and osmagents increase or decrease the solubility of a drug through manipulation of the drug's pH/solubility profile or by competing with the drug for water within the system. Buffers and osmagents, however, would be ineffective in delivery of poorly water-soluble drugs which have no acid-base character.

The usefulness of the above devices would be increased if a device and method were provided to improve the delivery of drugs which have been found to be difficult to incorporate into an osmotic drug delivery module without conversion of the parent drug into a new drug whose stability and toxicology are uncharacterized. Further utility results from methodology which provides for a sustaining of the improvement inducing effect through technology which substantially extends the lifetime of the modulating agent(s).

BRIEF DESCRIPTION OF DRAWINGS

FIG. 1 is a schematic representation of one embodiment of the instant invention. The device, 6, has a core composition comprised of drug(s), 3, solubility modulator(s), 2, surrounded by a rate modifying coat, 5, to form controlled release solubility modulating units that are dispersed among other excipients, 4, which may optionally contain elements found in 2, as needed to form a tablet suitable for the application of a microporous, rate-determining, water-insoluble wall, 1. In operation water permeates wall 1 at a rate controlled by the nature of wall 1, entering the core compartment where water soluble drug and excipients dissolve. The water then permeates coating 5 and the solubility modulator(s), 2, are metered through the coating, 5, into the core environment for a prolonged period where the solubility of drug, 3, is modified. A priming bolus of agent 2 may be provided in 4, to modulate the drug solubility during the lag-time for water and solution to permeate coat 5. Drug, 3, and those excipient and solubility modifiers which are dissolved in the core fluids are then freely permeable to exit the core compartment through wall 1 in response to osmotic and concentration gradients. It is often desirable for the lifetime of agent, 2, and drug, 3, to closely coincide to allow for solubility control throughout the entire delivery period of the drug. However, it is not a necessary requirement that the lifetimes of 2 and 3 be similar; in practice, lifetimes may be adjusted to achieve the kinetic profile of drug release best suited to the therapeutic need. Another embodiment of the present invention is schematically shown as device 8 in FIG. 1a. In this configuration the solubility modulator, 2, is dispersed throughout a matrix, 7, which acts as a carrier for the solubility modulator compound, 2. The solubility modulator, 2, is released from the matrix, 7, by mechanisms of dissolution, diffusion, partitioning, osmosis, or combinations thereof. Elements 1 through 4 were described previously.

OBJECT OF THE INVENTION

Figure 1:
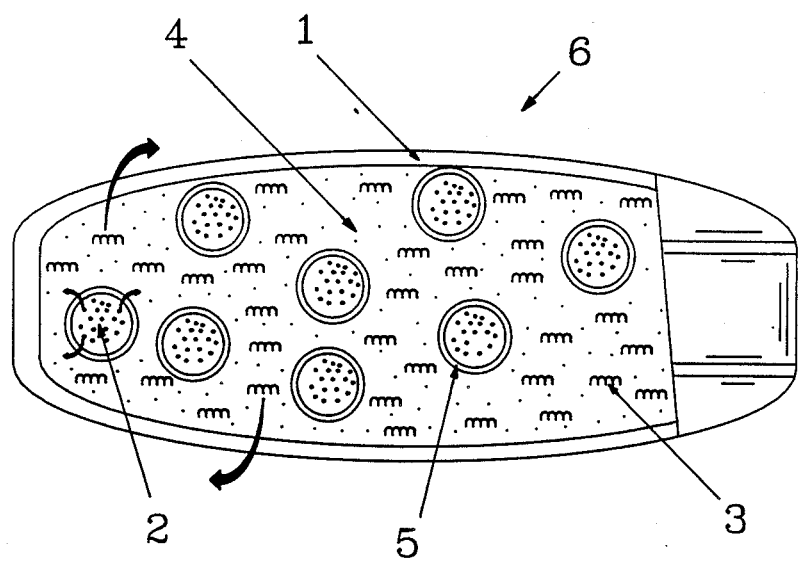
FIG. 1 is a schematic representation of one embodiment of the instant invention wherein the device, 6, has a core composition comprised of drug(s), 3, solubility modulator(s), 2, surrounded by a rate modifying coat, 5, to form controlled release solubility modulating units that are dispersed among other excipients, 4, which may optionally contain elements found in 2, as needed to form a tablet suitable for the application of a microporous, rate-determining, water-insoluble wall, 1.
Figure 1A:
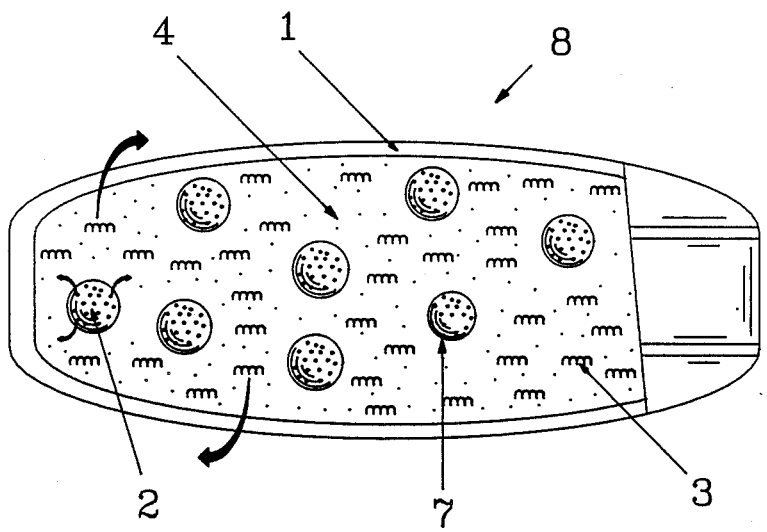
FIG. 1a is another embodiment of the present invention is schematically wherein the solubility modulator, 2, is dispersed throughout a matrix, 7, which acts as a carrier for the solubility modulator compound, 2.

It is an immediate object of this invention to provide a novel device for delivering an agent (drug) to produce a beneficial effect which overcomes the disadvantages associated with prior art devices.

Another object of the invention is to provide a device for delivering an agent at controlled rate over a specified period of time, which delivery is controlled by the device and not the environment surrounding the device.

Another object of the invention is to provide a device for controlled delivery of a drug and a solubility modulating agent where the solubililty, and thus delivery profile, of said drug is controlled by the drug-delivery device and not by the intrinsic water solubility of the drug.

Another object of the invention is to provide a method for converting unacceptable drug release profiles into profiles that have been recognized as therapeutically desirable. For example, drugs with intrinsic water solubilities that are very low will release from osmotic devices at slow rates that may be sub-therapeutic; modulation to increase the solubility of such drugs will increase the release rate into the therapeutic range. The above effects are achieved without chemical modification of the parent drug with attendant stability and toxicological concerns.

Another object of the invention is to provide a drug delivery device that is readily manufacturable to deliver a pre determined dose of agent at a programmed rate from compositions of matter in the varied geometries and sizes of tablets, pellets, multi-particulates, and such related dosage forms as familiar to those skilled in the art of oral, buccal, vaginal, rectal, nasal, ocular, aural, parenteral, and related routes of administration.

Another object of the invention is to provide a drug delivery device for delivering an active agent over a range of release rates as controlled by the device.

Other objects, features and advantages of the invention will be apparent to those skilled in the art from the following detailed description of the invention, taken in conjunction with the drawings and accompanying claims.

A device is disclosed for the delivery of a beneficial agent. The beneficial agent, commonly a drug, is delivered by osmotic pumping of dissolved drug, and excipients as required, at a controlled rate for a specified period to the environment surrounding the device. The solubility of the beneficial agent is controlled through the influence of a controlled release solubility modulator contained within the drug delivery device. The controlled release solubility modulator influences the release pattern of the beneficial agent. The device is comprised of (1) at least one beneficial agent, which can be poorly water soluble and (2) a controlled release solubility modulator selected from the group consisting of surfactants, or complexing agents which increase drug solubility. The controlled release solubility modulator can be either (i) surrounded by water insoluble coating containing pore forming additives dispersed throughout said coating or (ii) dispersed in an individual matrix substrate. Components (1) and (2) may be combined with excipients, binders, lubricants, glidants, and bulking agents as needed to form a core compartment of the device. The core is surrounded by a water insoluble microporous wall containing pore forming additive(s) dispersed througout said wall. In operation water is imbibed into the core compartment. As water enters the core it is further imbibed into the compartment(s) containing the controlled release solubility modulator. The contents of the solubility modulator compartment(s) are delivered into the surrounding environment where they modulate the solubility of the beneficial agent, thereby controlling the release of the beneficial agent from the device. By adjusting the amount and/or type of solubility modulator, the amount and/or type of coating or matrix applied to the solubility modulator, or amount and/or type of coating applied to the core compartment, the release profile of the device can be adjusted to meet the desired kinetic profile.

DETAILED DESCRIPTION OF THE INVENTION

The instat is directed to a drug-delivery device for the controlled release of a therapeutically active ingredient into an environment of use which comprises: Components (a) and (b) may be combined with excipients, binders, lubricants, glidants, and bulking agents as needed to form a core that is surrounded by a water insoluble, rate-determining wall containing at least one pore forming additive dispersed throughout said wall.

The term solubility modulating agent as used herein encompasses complexing agents and surfactants that can exert an effect on the solubility of the therapeutically active ingredient being delivered from the device. Complexation is a method for solubility modulation useful in the present invention. Complexes may be classified as metal ion complexes, organic molecular complexes, and occlusion compounds. Specific examples of complexing agents include but are not limited to sodium mandelate, 2-hydroxyphenyl acetic acid, 2-hydroxynicotinic acid, 3-hydroxy-3-phenyl propionic acid, phthalic acid, 3,4-dihydroxycinnamic acid cyclodextrins, polyethylene glycols, polyvinylpyrrolidone, sodium carboxymethylcellulose, tetracycline derivatives, caffeine, picric acid, quinhydrone, hydroquinone, sodium salicylate, salicyclic acid and mandelic acid. Another group of solubility modulating agents are surfactants. Generally, the surfactants are amphipathic molecules comprised of a hydrophobic part and a hydrophilic part. The surfactants can be anionic, cationic, nonionic or amphoteric. The anionic surfactants include sulfated, sulfonated, or carboxylate esters, amides, alcohols, ethers, aromatic hydrocarbons, aliphatic hydrocarbons, acylated amino acids and peptides. Metal alkyl phosphates are another class of anionic surfactants. Typically, cationic surfactants are primary, secondary, tertiary or quarternary alkylammonium salts, acylated polyamines, and salts of heterocyclic amines. Nonionic surfactants are typically esters and esters of polyoxyalkylene glycols, polyhydric alcohols, or phenols, Poloxeamars and poloxamines are included as nonionic surfactants. Surfactants are discussed in *Surfactant Systems. Their Chemistry, Pharmacy, and Biology*, D. Attwood and A. T. Florence, Chapman and Hall Pub Co., 1983. Examples of surfactants include potassium laurate, sodium alkylsulfates such as sodium dodecyl sulfate, hexadecylsulphonic acid, sodium dioctylsulphosuccinate, hexadecyl(cetyl)trimethylammonium bromide, dodecylpyridinium chloride, dodecylamine hydrochloride, N-dodecyl-N,N-dimethyl betaine, bile acids and salts, acacia, tragacanth, Igepal, polypxyethylated nonylphenols (liquid) sorbitan esters (Spans), polysorbates (Tweens), polyoxyethylated t-octylphenols (Triton-X-analogs)-polyoxyethylene lauryl ethers, polyoxyethylene cetyl ethers, polyoxyethylene stearyl ethers, polyoxyethylene oleyl ethers (Brij analogs, polyoxyethylene stearate Myrj analogs, pluronics, tetronics, poloxamer and poloxamine type polyoxyethylene-polyoxypropylene derivatives (Pluronics and Tetronics) surface active drug agents such as phenothiazines and tricyclic antidepressants, and the like.

The solubility modulating agent can be surrounded by a water insoluble, permeable, coat that contains at least one pore forming additive dispersed throughout said coat. This coat is often applied to the solubility modulating agent by spray-coating procedures. A portion of the solubility modulating agent may be left uncoated to effect immediate availability during the period intervening the onset of release from the controlled release solubility modulating element(s). The solubility modulating agent can also be incorporated into individual matrix units; incorporation effects a controlled release of said agent. Other excipients may also be combined with beneficial agent (drug) and solubility modulating agent(s) as needed to maintain pH, promote stability, facilitate manufacturability ability, and provide osmotic activity to the dissolved core compartment solution to effect a desirable release profile. The entire composite is compressed or formed into tablets, beads, multi-particulates, and the like, by conventional methodology to form cores onto which a water insoluble wall containing leachable pore forming additives is applied. Thus, the finished device may contain solubility modulators in the various form of either: (a) coated solubility modulator; (b) solubility modulator dispersed in a matrix; (c) immediate availability solubility modulator, or (d) mixtures of (a), (b) and (c), within the core compartment which is then surrounded by a porous wall.

The walls or coatings are comprised of (a) polymeric materials that are insoluble in the fluids of the environment of intended use (usually agueous), (b) other added excipients that will dissolve in the environmental fluids or leach out of the walls. The leached walls are spongelike structures composed of numerous open and closed cells that form a discontinuous interwoven network of void spaces when viewed with a scanning electron microscope. These controlled porosity walls serve as both water entry and core composition solution exit sites. The walls are permeable to both water and solutes, and as constituted in the environment of use have a small solute reflection coefficient, o and display poor semipermeable characteristics when placed in a standard osmosis cell.

The specifications for the wall are summarized below and include:
1. Fluid Permeability of the wall: $6.96 \times 10^{-18}$ to $6.96 \times 10^{-14}$ cm$^3$ sec/g (equivalent to $10^{-5}$ to $10^{-1}$ cm$^3$ mil/cm$^2$ hr atm).
2. Reflection Coefficient: Microporous coats to have a reflection coefficient, $\sigma$, defined as:

$$\sigma = \frac{\text{osmotic volume flux} \times \text{hydrostatic pressure difference}}{\text{osmotic pressure difference} \times \text{hydrostatic volume flux}}$$

where $\sigma$ is less than 1, usually 0 to 0.8.

Additional, preferred specifications for the wall include:
1. Plasticizers and Flux Regulating Additives: 0 to 50, preferably 0.001 to 50, parts per 100 parts wall material.
2. Surfactant Additives: 0 to 40, preferably 0.001 to 40, parts per 100 parts wall material.
3. Wall Thickness: 1 to 1,000, preferably 20 to 500, microns typically although thinner and thicker fall within the invention.
4. Microporous Nature: 5% to 95% pores between 10 angstroms and 100 microns diameter.
5. Pore Forming Additives: 0.1 to 75%, preferably 0.1 to 50%, by weight, based on the total weight of pore forming additive and polymer, pore forming additive, preferably: a) 0.1 to 50%, preferably 0.1 to 40%, by weight solid additive; b) 0.1 to 40% by weight liquid additive, but no more than 75% total pore formers.

The water insoluble wall of the instant invention must not be covered on its inner or outer surface by a layer of material that is impermeable to dissolved solutes within the core during the period of operation.

Any polymer permeable to water but impermeable to solutes as previously defined may be used. Examples include cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate having an acetyl content of 2 to 99.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate, methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate, beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethyl cellulose, hydroxylated ethylenevinyl acetate, poly(ortho ester)s, polyacetals, semipermeable polyglycolic or polylactic acid and derivatives thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, polyacrylate and polymethacrylate polymers, and derivatives and the like. Admixtures of various polymers may also be used.

The polymers described are known to the art or they can be prepared according to the procedures in Encyclopedia of Polymer Science and Technology, Vol. 3, pages 325 to 354, and 459 to 549, published by Interscience Publishers, Inc., New York, in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

A controlled porosity wall can be generically described as having a sponge like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used.

Pore forming additives may be used in the instant invention. The microporous wall may be formed in situ, by a pore former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers that can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like; the alkaline earth metal salts such as calcium chloride, calcium nitrate, and the like; the transition metal salts such as ferric chloride, ferrous sulfate, zinc sulfate, cupric chloride, and the like. Water may be used as the pore-former. The pore-formers include organic compounds such as dimethyl sulfone, nicotin amide, saccharides and amino acids. The saccharides include the sugars sucrose, glucose, fructose, mannose, galactose, aldohexose, altrose, talose, lactose, monosaccharides, disaccharides, and water soluble polysaccharides. Also, sorbitol, pentaerythritol mannitol, organic aliphatic and aromatic ols, including diols and polyols, as exemplified by polyhydric alcohols, poly(alkylene glycols), polyglycols, alkylene glycols, poly($\alpha,\omega$)alkylenediols esters or alkylene glycols, polyvinylalcohol, polyvinylpyrralidone, and water soluble polymeric materials. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore-formers are nontoxic, and on their removal channels are formed that fill with fluid. The channels become a transport path for fluid. In a preferred embodiment, the non-toxic pore-forming agents are selected from the group consisting of water soluble inorganic and organic compounds and salts, carbohydrates, polyalkylene glycols, poly($\alpha,\omega$) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes: A Structural Perspective*, 2nd Ed., by R. E. Kesting, Chapters 7 and 8, 1985, published by John Wiley & Sons, Inc.; *Chemical Reviews, Ultrafiltration*, Vol. 18, pages 373 to 455, 1934; *Polymer Eng. and Sci.*, Vol. 11, No. 4, pages 284 to 288, 1971, *J. Appl. Poly. Sci.*, Vol. 15, pages 811 to 829, 1971, and in U.S. Pat. Nos. 3,565,259; 3,615,024; 3,751,536; 3,801,692; 3,852,224; and 3,849,528.

It is generally desirable from a preparation standpoint to mix the polymer in a solvent. Exemplary solvents suitable for manufacturing the wall of the instant device include inert inorganic and organic solvents that do not adversely harm the core, wall, and the materials forming the final wall. The solvents broadly include members selected from the group consisting of agueous solvents, alcohols, ketones, esters, ethers, aliphatic hydrocarbons, halogenated solvents, cycloaliphatic, aromatics, heterocyclic solvents and mixtures thereof. Water based latex forms of the suitable polymers also fall within the scope of the invention. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl ethyl ketone, methyl propyl ketone, n-hexane, ethyl lactate, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethylbromamide, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Illustrative of mixed solvents are acetone-methanol (80:20), acetoneethanol (90:10), methylene dichloride-methanol (80:20), ethyl acetate-ethanol (80:20), ethylene dichloride-methanol (80:20), methylene dichloride-methanol (50:50), methylene dichloride-methanol (78:22), acetone-water (90:10), chloroform-ethanol (80:20), methylene dichloride-ethanol (79:21), methylene chloride-methanol water (15:10:1), carbontetrachloride-methanol (70:30), expressed as (weight:weight), and the like. Water-based latex forms of suitable polymeric materials are also within the scope of the invention.

Exemplary plasticizers suitable for the present purpose include plasticizers that lower the temperature of the second-order phase transition of the wall or the elastic modulus thereof, and also increase the workability of the wall and its flexibility. Plasticizers may increase or decrease the permeability of the wall to fluids including water and aqueous solutions. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, polyethylene glycols, polypropylene glycols, and halogenated phenyls. Generally, from 0.001 to 50 parts of a plasticizer or a mixture of plasticizers are incorporated into 100 parts of wall forming material.

Exemplary plasticizers include dialkyl phthalates, dicycloalkyl phthalates, diaryl phthalates and mixed alkylaryl as represented by dimethyl phthalate, dipropyl phthalate, dioctyl phthalate, di-(2-ethyl-hexyl)-phthalate, di-isopropyl phthalate, diamyl phthalate and dicapryl phthalate; alkyl and aryl phosphates such as triethyl phosphate, tributyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di-(2-methyoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol dibutyrate and triethylene glycol dipropionate. Other plasticizers include polyethylene glycol 400, polyethylene glycol 20,000, camphor, N ethyl (o- and p-toluene) sulfonamide, chlorinated biphenyl, benzophenone, N-cyclohexyl-p toluene sulfonamide, and substituted epoxides.

Suitable plasticizers can be selected for blending with the wall forming materials by selecting plasticizers that have a high degree of solvent power for the materials, are compatible with the materials over both the processing and use temperature range, exhibit permanence as seen by their tendency to remain in the plasticized wall, impart flexibility to the material and are non-toxic to animals, humans, avians, fishes and reptiles. Procedures for selecting a plasticizer having the described characteristics are disclosed in the *Encyclopedia of Polymer Science and Technology,* Vol. 10, pages 228 to 306, 1969, published by John Wiley & Sons, Inc. Also, a detailed description pertaining to the measurement of plasticizer properties including solvent parameters and compatibility such as the Hildebrand solubility para-meter $\delta$, the Flory-Huggins interaction parameter X, and the cohesive energy density, CED, parameters are disclosed in *Plasticization and Plasticizer Processes, Advances in Chemistry Series* 48, Chapter 1, pages 1 to 26, 1965, published by the American Chemical Society. The amount of plasticizer added generally is an amount sufficient to produce the desired wall and it will vary according to the plasticizer and the other wall forming materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability (flux) through the wall. The agent can be preselected to increase or decrease the fluid flux. Agents that produce a marked increase in permeability to a fluid such as water, are often essentially hydrophilic, while those that produce a marked decrease in permeability to fluids such as water, are often essentially hydrophobic. The flux regulators in some embodiments also can increase the flexibility and porosity of the lamina.

Examples of flux regulators include poly hydric alcohols and derivatives thereof, such as polyalkylene glycols of the formula $H-(O-\text{alkylene})_n-OH$, wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula $H-(OCH_2CH_2)_n-OH$ wherein n is typically 5 to 5.7, 8.2 to 9.1, 12.5 to 13.9, 29 to 36, 29.8 to 37, 68 to 84, and 158 to 204, respectively. Other polyglycols include the low molecular weight glycols of polypropylene, polybutylene and polyamylene.

Additional flux regulators include poly ($\alpha,\omega$) alkylenediols wherein the alkylene is straight or branched chain of from 2 to 10 carbon atoms such as poly(1,3)-propanediol, poly(1,4) butanediol, poly(1,5)pentanediol and poly(1,6)hexanediol. The diols also include aliphatic diols of the formula $HOC_nH_{2n}OH$ wherein n is from 2 to 10 and diols are optionally bonded to a nonterminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO—(alkylene-O)$_n$—H wherein the divalent alkylene radical includes the straight chain groups and the isomeric forms thereof having from 2 to 6 carbons and n is 1 to 14. The esters and polyesters are formed by reacting the glycol with either a monobasic or dibasic acid or anhydride. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Surfactants useful for the present coat forming purpose are those surfactants, when added to a wall forming material and other materials, aid in producing an integral composite that is useful for making the operative wall of a device. The surfactants act by regulating the surface energy of materials to improve their blending into the composite. The composite material is used for manufacturing devices that maintain their integrity in the environment of use during the agent release period. Generally, the surfactants are amphipathic molecules comprised of a hydrophobic part and a hydrophilic part. The surfactants can be anionic, cationic, nonionic or amphoteric. The anionic surfactants include sulfated, sulfonated, or carboxylated esters, amides, alcohols, ethers, aromatic hydrocarbons, aliphatic hydrocarbons, acylated amino acids and peptides. Metal alkyl phosphates are another class of anionic surfactant. Typically, cationic surfactants are primary, secondary, tertiary or quaternary alkylammonium salts, acylated polyamines, and salts of heterocyclic amines. Nonionic surfactants are typically esters and ethers of polyoxyalkylene glycols, polyhydric alcohols, or phenols. Poloxamers are included as nonionic surfactants. Ampholytic molecules such as betaine are also surfactants. Surfactants are discussed in *Surfactant Systems, Their Chemistry, Pharmacy, and Biology,* D. Attwood and A. T. Florence, Chapman and Hall Pub. Co., 1983, pgs 1–8.

Examples of surfactants include potassium laurate, sodium dodecyl sulfate, hexadecylsulphonic acid, sodium dioctylsulphosuccinate, hexadecyl(cetyl)trimethylammonium bromide, dodecylpyridinium chloride, dodecylamine hydrochloride, N-dodecyl-N,N-dimethyl betaine, bile acids and salts, acacia, tragacanth, Igepal, sorbitan esters (Spans), polysorbates (Tweens), Triton-X analogs, Brij analogs, Myrj analogs, pluronics, tetronics, surface active drug agents such as phenothiazines and tricyclic antidepressants, and the like.

Suitable surfactants can be selected from the above and from other surfactants for blending with wall forming materials by using the surfactant's hydrophile-lipophile balance number, HLB. This number represents the proportion between the weight percent ages of hydrophilic and lipophilic groups in a surfactant. In use, the number indicates the behavior of the surfactant, that is, the higher the number the more hydrophilic the surfactant and the lower the number the more lipophilic the surfactant. The required HLB number for blending wall forming materials is determined by selecting a surfactant with a known HLB number, blending it with the materials and observing the results. A uniform composite is formed with the correct HLB number, while a non uniform mixture indicates a different number is needed. This new number can be selected by using the prior HLB number as a guide. The HLB number is known to the art for many surfactants, and they can be experimentally determined. Generally a HLB number of 10 or less indicates lipophilic behavior and 10 or more indicates hydrophilic behavior. Also, HLB numbers are algebraically additive. Thus, by using a low number with a high number, blends of surfactant can be prepared having numbers intermediate between the two numbers. The concept of HLB is detailed in *Remington's Pharmaceutical Sciences,* 16th Ed., Mack Pub. Co., (1980), pages 316–319. The amount of surfactant needed is an amount that when blended with wall forming materials will form the desired wall composite, and it will vary according to the particular surfactant and materials that are blended to form the wall. Generally, the amount of surfactant will range from about 0.001 part up to 40 parts for 100 parts of wall.

Materials suitable as matrix materials for dispersing the solubility modulating agents include those described previously for use as coating materials. Additional appropriate matrix materials include materials that are semisolid to solid that dissolve or erode within the fluid which forms within the core in the environment of use, or insoluble materials that serve as diffusion media to modulate the leaching of the solubility modulator into the core compartment fluids. Specific examples include, but are not limited to hydroxypropyl cellulose, hydroxypropylmethyl cellulose, solid polyethylene glycols, carboxypolymethylene, silicone rubber, pectin ethylene vinyl acetate, waxes, fats, fatty acids, fatty alcohols, triglycerides, natural gums, polylactic acid, poly(ortho ester)s, and the like.

The terms drug and beneficial agent and therapeutically active agent includes any compound, or mixture thereof, that can be delivered from the device to produce a beneficial result. The terms include pesticides, herbicides, germicides, biocides, algicides, rodenticides, funqicides, insecticides, antioxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, and other agents that benefit the environment of use.

In the specification and the accompanying claims, the terms drug, beneficial agent and therapeutically active agent "drug" includes any physiologically or pharmacologically active substances that produce a localized or systemic effect or effects in animals, which term includes mammals, humans and primates. The term also includes domestic household, sport or farm animals such as sheep, goats, cattle, horses and pigs, for administering to laboratory animals such as mice, rats and guinea pigs, and to fish to avians, to reptiles and zoo animals. The term "physiologically" as used herein denotes the administration of drug to produce desirable levels and functions. The term "pharmacologically" denotes the study of the actions of drugs on living systems, including therapeutics, as defined in *Dorland's*

*Illustrated Medical Dictionary,* 1974, published by W. B. Saunders Co., Philadelphia, Pa. The phrase drug formulation as used herein means the drug is in the compartment by itself, or the drug is in the compartment mixed with an osmotic solute, binder, dye, solubility modulator, excipients, mixtures thereof, and the like. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synaptic sites, neuroeffector junctional sites, endocrine and hormone systems, immunological system, reproductive system, skeletal system, autocoid systems, alimentary and excretory systems, inhibitory or autocoids and histamine systems, and those materials that act on the central nervous system such as hypnotics and sedatives.

Examples of beneficial druqs are disclosed in *Remington's Pharmaceutical Sciences,* 17th Ed., 1985, published by Mack Publishing Co., Eaton, Pa.; and in *The Pharmacological Basis of Therapeutics,* by Goodman and Gilman, 6th Ed., 1980, published by the MacMillan Company, London; and in *The Merck Index,* 10th Edition, 1983, published by Merck & Co., Rahway, N.J. The drug can be in various forms, such as neutral or charged molecules, neutral or charged molecular complexes or associations, or ionizable salts. Acceptable salts include, but are not limited to hydrochlorides, hydrobromide, sulfate, laurylate, palmitate, phosphate, nitrate, borate, acetate, maleate, tartrate, oleate, salicylate malate, ammonium, tromethamine, salts of metals, and amines or organic cations, for example quaternary ammonium.

Derivatives of drugs such as esters, ethers and amides which have ionization and solubility characteristics suitable for use herein can be used alone or mixed with other drugs which upon release from the device, are converted by enzymes, hydrolyzed by body pH or other metabolic processes to the original form, or to a biologically active form.

Specific examples of drugs that may be adapted for use include diazepam, levodopa/carbidopa, α-methyldopa, indomethacin, sulindac, diflunisal, prostaglandins, invermectin, dexamethasone, norethindrone, norgestrel, ethinyl estradiol, hydrochlorothiazide, timolol, norfloxacin, theophylline, haloperidol, nifedipine, digoxin, enalapril, lisinopril ranitidine, famotidine, lovastatin, simvastatin, pravistatin, and milbemycin.

The preferred specifications for the core are summarized below and include:
1. Core Druq Loading (size): 0.05 nano grams to 5 qrams or more (includes dosage forms for humans and animals).
2. Osmotic pressure developed by a solution of the core: 8 to 500 atmospheres, typically, with commonly encountered drugs and excipients; however osmotic pressures greater than zero are within quidelines.
3. Core solubility: continuous, uniform release (zero-order kinetics) of 90% or greater of the initially loaded core mass is theoretically predicted if the ratio of the dissolvable core mass solubility, S, to the dissolvable core mass density, $\rho$, that is $S/\rho$, is 0.1 or lower. Typically this occurs when 10% of the initially loaded dissolvable core mass saturates a volume of external fluid equal to the total volume of the initial dissolvable core mass.

$S/\rho$ ratios greater than 0.1 fall within the workings of the invention and result in lower percentages of initial core mass delivered under zero-order kinetics $S/\rho$ can be selected to give acceptable combined characteristics of stability, release rate, and manufacturability.

4. Controlled Release Solubility Modulator: 0.01 to 75%, by weight, of the total core mass.

There is no critical upper limit as to the amount of drug that can be incorporated into a core mass and typically will follow the core loading (size) specification 1. The lower limit ratio of drug to excipient is dictated by the desired drug solubility desired osmotic activity of the core composition, the desired time span and profile of release, and the pharmacological activity of the drug. Generally, the core will contain 0.01% to 90% by weight or higher, of an active agent in mixture with another solute(s). Representative of compositions of matter that can be released from the device and can function as a solute are, without limitation, those compositions soluble in fluids inside the core compartment as described.

The following examples illustrate the preparation of the drug-delivery devices of this invention and their controlled release of one or more therapeutically active ingredients into an enviroment of use and as such are not to be considered as limiting the invention set forth in the claims appended hereto.

EXAMPLES

In the following examples the hydroxymethylglutaryl-coenzyme A reductase inhibitors (HMG CoA reductase inhibitors) simvastatin and lovastatin are used as model drugs. These drugs are highly effective in the reduction of blood cholesterol levels in humans and possess neither acidic nor basic functionality. The aqueous solubilities of simavastatin and lovastatin are 0.03 mg/ml and 0.00044 mg/ml respectively, at 20° C. Their very low water solubilities would preclude the incorporation of these drugs into conventional osmotic controlled release drug-delivery devices. The solubility modulating properties of surfactants and complexing agents increase the total solubilities of simavastatin and lovastatin and permit the successful formulation of intrinsically water-insoluble drugs into controlled-release osmotic drug-delivery devices, as disclosed in the following Examples.

EXAMPLE 1

A plurality of solubility modulated osmotic drug-delivery devices containing controlled release sodium dodecyl sulfate (C.R SDS) surfactant particles to modulate the solubility of simvastatin are prepared. The C.R. SDS is manufactured by first granulating 300 g lactose mixed with 300 g SDS in a fluid-bed granulator to form SDS granules. The granulating fluid consists of 36 g polyvinylpyrrolidone 29–32K dissolved in 100 ml ethanol. The SDS granules are dried in a convection oven at 50° C. These granules are sized through a #18 sieve (1.0 mm opening) and a microporous wall is then applied to these granules by standard fluidized-bed spray coating techniques. The microporous coat spray solution is cellulose acetate butyrate 381-20 (I00 grams) dissolved in an acetone:-methanol (3.1) solvent blend. To this is added 50 g sorbitol as a pore former dissolved in a methanol:water (3:1) solvent blend. This solution is sprayed onto the SDS granules in a commercial Uni-Glatt ® fluidized-bed coating machine. The SDS granules are coated to a thickness sufficient to give 4–24 hours of continuous release of SDS into 37° C. water as measured by a Jenway PCM3 conductivity meter. Next, a wet granulation is prepared containing simvastatin, mannitol, sodium dodecyl sulfate, and C.R. BDS mixed 1:10:1.5:2.5. The granulating fluid consists of 9% w/w polyvinylpyrrolidone 29–32K dissolved in ethanol. The granules are dried in a convection oven at 45° C. These granules are formed into core tablets by compressing 330 mg aliquots (20 mg drug load) into a ⅜" deep concave tableting die on a Manesty ® tablet press. Next, a microporous coat is applied to these cores. 72 g cellulose acetate butyrate 318-20 is dissolved in an acetone/methanol solvent blend. To this is added 72 g sorbitol as pore former dissolved in a water/methanol solvent blend. This solution is sprayed onto the cores in a commercial Uni-Glatt ® fluidized coating machine to form a wall of sufficient thickness to provide a continuous release of simvastatin into pH 7.4 phosphate buffered saline at 37° C. for an extended period of from 4 to 24 hours.

EXAMPLE 2

The procedures outlined in Example 1 are repeated with the exception that the C.R. SDS particles are manufactured as a matrix rather than as coated particulates. The C.R. SDS matrix particles are prepared by granulating 300 g SDS with 300 g lactose. The granulating fluid consists of Methocel K4M-Premium ® (hydroxypropylmethylcellulose) dissolved in a water:ethanol solvent blend. These granules are dried in convection oven at 50° C. The resulting C.R. SDS matrix particles release sodium dodecyl sulfate (SDS) for an extended period which may be increased through increases in the weight percent ratio of Methocel K4M-Premium ® to SDS/lactose.

EXAMPLE 3

A plurality of solubility modulated osmotic drug-delivery systems containing controlled release sodium salicylate (complexing agent) particles to modulate the solubility of lovastatin are prepared. The controlled release sodium salicylate (C.R. NaSal) is manufactured by granulating a 700 g aliquot of sodium salicylate in a fluidized-bed granulator. The granulating fluid consists of 36 g polyvinylpyrrolidone 29–32K dissolved in 100 ml ethanol. The granules are dried in a convection oven at 50° C. These granules are then sized through a #18 sieve (1.0 mm opening) and a microporous wall is then applied to these granules by standard fluidized-bed spray coating techniques. The spray solution is 100 g cellulose acetate butyrate 381-20 dissolved in a 3:1 acetone:methanol solvent blend. To this is added 50 g sorbitol as a pore former in a methanol:water (3:1) solvent blend. This solution is then sprayed onto the sodium salicylate granules in a commercial Uni-Glatt ® fluidized-bed coating machine. The sodium salicylate granules are coated to a thickness sufficient to give 4–24 hours of continuous release of sodium salicylate into water (37°C.) as measured by HPLC. Next, a wet granulation is prepared containing lovastatin, sodium salicylate and C.R. NaSal mixed 1:2.5:1.25. The granulating fluid consists of 5% w/w polyvinylpyrrolidone 29–32K dissolved in ethanol. These granules are dried in a convection oven at 45° C. This mixture of granules is lubricated with 0.5% by weight magnesium stearate and compressed into 200 mg core tablets (40 mg lovastatin) in a ¼" standard concave tableting die on a Manesty ® tablet press. Next, a microporous coat is applied to these cores. 72 g cellulose acetate butyrate 381-20 is dissolved in an acetone/ methanol solvent blend. To this is added 72 g sorbitol as pore former dissolved in a water/methanol solvent blend. This solution is sprayed onto the cores in a commercial Uni-Glatt ® fluidized-bed coating machine to form a wall of sufficient thickness to provide a continuous release of lovastatin into pH 7.4 phosphate buffered saline at 37° C. for an extended period of from 4 to 24 hours.

EXAMPLE 4

The procedure outlined in Example 3 are repeated with the exception that the C.R. NaSal particles are manufactured as a matrix rather than as coated particulates. The C.R. NaSal is prepared by granulating 500 g sodium salicylate mixed with 200 g lactose and 75 g cornstarch. The granulating fluid consists of Methocel K4M-Premium ® (hydroxypropylmethylcellulose) dissolved in a water/ethanol solvent blend. These granules are dried in a convection oven at 50° C. The resulting C.R. NaSal matrix particles release for an extended period which may be increased through increases in the weight percent ratio of Methocel K4M-Premium ® to sodium salicylate/lactose/cornstarch.

What is claimed is:

1. A drug-delivery device for the controlled release of a therapeutically active ingredient into an environment of use which comprises:
   (A) a core composition comprising
      (a) a plurality of controlled release solubility modulating units which modulate and increase solubility of said therapeutically active ingredient within said core comprising solubility modulating agents each of which is either a complexing agent or a surfactant and which is
         (i) surrounded by a water insoluble coat containing at least one pore forming additive dispersed throughout said coat, or
         (ii) dispersed in an individual matrix substrate, and
      (b) a therapeutically active ingredient; and
   (B) a water insoluble microporous wall surrounding said core composition and prepared from
      (i) a polymer material that is permeable to water but substantially impermeable to solute and
      (ii) 0.1 to 75% by weight, based on the total weight of (i) and (ii), of at least one water leachable pore forming additive dispersed throughout said wall.

2. A drug-delivery device according to claim 1, wherein the solubility modulating agent is an acid or base selected for adipic acid, citric acid, fumaric acid, tartaric acid, succinic acid, sodium phosphates, potassium phosphates, calcium phosphate, ammonium phosphate, magnesium oxide, magnesium hydroxide, sodium tartrate, tromethamine.

3. A drug-delivery device according to claim 1, wherein the solubility modulating agents are dispersed in individual matrix substrates.

4. A drug delivery device according to claim 1, wherein the therapeutically active agent is selected from the group consisting of lovastatin and simvastatin.

5. A drug-delivery device according to claim 1, wherein the solubility modulating agent is a complexing agent selected from cyclodextrins, polethylene glycols, polyvinylpyrrolidone, sodium carboxymethylcellulose, salicylic acid, sodium salicylate, mandelic acid, sodium mandelate, caffeine, picric acid, quinhydrone, hydroquinone and tetracycline derivatives, and 2-hydroxyphenyl acetic acid, 2-hydroxynicotinic acid, 3- hydroxy-3-phenyl propionic acid, phthalic acid, 3-4-dihydroxycinnamic acid and the corresponding sodium salts.

6. A drug-delivery device according to claim 1, wherein the solubility modulating agent is surfactant selected from potassium laurate, sodium dodecyl sulfate, hexadecylsulphonic acid, sodium dioctylsulphosuccinate, hexadecyl(cetyl)-trimethylammonium bromide, dodecylpyridinium chloride, dodecylamine hydrochloride, N-dodecyl-N,N-dimethyl betaine, acacia, tragacanth, Igepal, sorbitan esters, polysorbates, Triton-X analogs, Brij analogs, Myrj analogs, pluronics, tetronics, bile salts, bile acids, sulfated, sulfonated, or carboxylated esters, amides, alcohols, ethers, aromatic hydrocarbons, aliphatic hydrocarbons, acylated amino acids and peptides, metal alkyl phosphates, primary, secondary, tertiary or quaternary alkylammonium salts, acylated polyamines, salts of heterocyclic amines, and ethers of polyoxyalkylene glycols, polyhydric alcohols or phenols.

7. A method modulating the controlled release of a therapeutically active ingredient into an environment of use which comprises introducing into an environment of use:
   (A) a core composition comprising:
      (a) a plurality of controlled release solubility modulating units which modulate and increase solubility of said therapeutically active ingredient within said core comprising solubility modulating agents each of which is a complexing agent or a surfactant and which is either (i) surrounded by a water insoluble coat containing at least one pore forming additive dispersed throughout said coat, or (ii) dispersed in an individual matrix substrate, and
      (b) a therapeutically active ingredient; and
   (B) a water insoluble microporous wall surrounding said core composition and prepared from
      (i) a polymer material that is permeable to water but substantially impermeable to solute and
      (ii) 0.1 to 75% by weight, based on the total weight of (i) and (ii), of at least one water leachable pore forming additive dispersed throughout said wall; thereby increasing the solubility of said therapeutically active agent and releasing into said environment of use associations of said therapeutically active ingredient and solubility modulating agents.

8. A drug deliver device for the controlled release of a therapeutically active ingredient having not appreciable acid-base character into an environment of use comprising:
   (A) a core composition comprising:
      (a) a plurality of controlled release solubility modulating units comprising solubility modulating agents each of which is a complexing agent or a surfactant and which is either (i) surrounded by a water insoluble coat containing at least one pore forming additive dispersed throughout said coat, or (ii) dispersed in an individual matrix substrate, and
      (b) A therapeutically active ingredient; and
   (B) a water insoluble microporous wall surrounding said core composition comprising:
      (i) a polymer material that is permeable to water but substantially impermeable to solute and
      (ii) 0.1 to 75% by weight, based on the total weight of (i) and (ii), of at least one water leachable pore forming additive dispersed throughout said wall.

* * * * *

UNITED STATES PATENT AND TRADEMARK OFFICE
CERTIFICATE OF CORRECTION

PATENT NO. : 4,946,686
DATED : August 7, 1990
INVENTOR(S) : Gregory A. McClelland & Gaylen M. Zentner It is certified that error appears in the above-identified patent and that said Letters Patent is hereby corrected as shown below:

At Column 1, line 47, line 49 and line 55 "gastro-intestinal" should be deleted and --gastrointestinal-- inserted therefor.

At Column 3, line 52, "pre determined" should be deleted and -- pre-determined -- inserted therefor.

At Column 4, line 38, "instat" should be deleted and -- instant invention -- inserted therefor.

At Column 4, line 40, after "comprises:" insert (A) a core composition comprising (a) a plurality of controlled release solubility modulating units comprised of solubility modulating agents each of which a complexing agent or a surfactant and which is either (i) surrounded by a water insoluble coat containing at least one pore forming additive dispersed throughout said coat, or (ii) dispersed in an individual matrix substrate, and

UNITED STATES PATENT AND TRADEMARK OFFICE
CERTIFICATE OF CORRECTION

PATENT NO. : 4,946,686

DATED : August 7, 1990

INVENTOR(S) : Gregory A. McClelland & Gaylen M. Zentner

It is certified that error appears in the above-identified patent and that said Letters Patent is hereby corrected as shown below:

(b) A diffusible water soluble therapeutically active ingredient; and (B) a water insoluble microporous wall surrounding said core composition and prepared from (i) a polymer material that is permeable to water but substantially impermeable to solute and (ii) 0.1 to 75% by weight, based on the total weight of (i) and (ii), of at least one water leachable pore forming additive dispersed throughout said wall.

At Column 4, line 67, "carboxylate" should be deleted and -- carboxylated -- inserted therefor.

At Column 5, line 6, after "and" delete "esters" and insert -- ethers --.

UNITED STATES PATENT AND TRADEMARK OFFICE
CERTIFICATE OF CORRECTION

PATENT NO. : 4,946,686

DATED : August 7, 1990

INVENTOR(S) : Gregory A. McClelland & Gaylen M. Zentner

It is certified that error appears in the above-identified patent and that said Letters Patent is hereby corrected as shown below:

At Column 5, lines 7 and 8 delete, "Polox-eamars" and insert therefor -- Poloxamers --.

At Column 5, line 18, delete "Igepal" and insert therefor -- (Igepal) --.

At Column 5, line 18, delete "polypxyethylated" and insert therefor -- polyoxyethylated --.

At Column 5, line 19 delete, "(liquid)" and insert therefor -- (Igepal) --.

At Column 5, line 23, after "(Brij analogs" insert therefor --)--.

At Column 5, line 24, delete "stearate" and insert -- stearates --.

At Column 5, line 24, delete "Myrj analogs" and insert therefor -- (Myrj analogs) --.

At Column 5, line 24, delete "pluronics, tetronics".

UNITED STATES PATENT AND TRADEMARK OFFICE
CERTIFICATE OF CORRECTION

PATENT NO. : 4,946,686

DATED : August 7, 1990

INVENTOR(S) : Gregory A. McClelland & Gaylen M. Zentner

It is certified that error appears in the above-identified patent and that said Letters Patent is hereby corrected as shown below:

At Column 5, line 59, delete "agueous" and insert -- aqueous --.

At Column 6, line 1, delete "0" and insert therefor -- $\sigma$ --.

At Column 7, line 47, delete "3,173,876".

At Column 8, line 30, delete "polyvinylpyrralidone" and insert -- polyvinylpyrrolidone --.

At Column 9, line 3, delete "agueous" and insert -- aqueous --.

At Column 12, line 47, delete "funqicides" and insert therefor -- fungicides --.

At Column 13, line 49, after "and milbemcycin" insert

-- The above list of drugs is not meant to be exhaustive. Many other drugs will certainly work in the instant invention.

UNITED STATES PATENT AND TRADEMARK OFFICE
CERTIFICATE OF CORRECTION

PATENT NO. : 4,946,686

DATED : August 7, 1990

INVENTOR(S) : Gregory A. McClelland & Gaylen M. Zentner

It is certified that error appears in the above-identified patent and that said Letters Patent is hereby corrected as shown below:

The drug can be in the core compartment as a solution, dispersion, paste, cream, particle, granule, emulsion, suspension or powder. Also, the drug can be mixed with a binder, dispersant, emulsifier or wetting agent and dyes.

The core compartment containing the drug and the controlled release solubility modulator, as described herein, is typically in the form of a solid conventional tablet, pellet or particulate. The core can be comprised of a mixture of agents combined to give the desired manufacturing and delivery characteristics. The number of agents that may be combined to make the core is substantially without an upper limit with the lower limit equalling two components. It may be useful to buffer the core compartment to control the electrostatic charge of the drug. --

At Column 13, line 52, delete "Druq" and insert therefor -- Drug --.

UNITED STATES PATENT AND TRADEMARK OFFICE
CERTIFICATE OF CORRECTION

PATENT NO. : 4,946,686

DATED : August 7, 1990

INVENTOR(S) : Gregory A. McClelland & Gaylen M. Zentner

Page 6 of 8

It is certified that error appears in the above-identified patent and that said Letters Patent is hereby corrected as shown below:

At Column 13, line 53, delete "qrams" and insert therefor -- grams --.

At Column 14, line 62, delete "(I00 grams)" and insert -- (100 grams) --.

At Column 15, line 4, delete "BDS" and insert therefor -- SDS --.

At Column 15, line 12 delete "318-20" and insert therefor -- 381-20 --.

At Column 16, line 48 delete

"A drug-delivery devise according to claim 1, wherein the solubility modulating agent is an acid or base selected for adipic acid, citric acid, fumaric acid, tartaric acid, succinic acid, sodium phosphates, potassium phosphates, calcium phosphate, ammonium phosphate, magnesium oxide, magnesium hydroxide, sodium tartrate, tromethamine."

and insert therefor

UNITED STATES PATENT AND TRADEMARK OFFICE
CERTIFICATE OF CORRECTION

PATENT NO. : 4,946,686

DATED : August 7, 1990

INVENTOR(S) : Gregory A. McClelland & Gaylen M. Zentner

It is certified that error appears in the above-identified patent and that said Letters Patent is hereby corrected as shown below:

-- A drug-delivery device according to Claim 1, wherein the solubility modulating agent is surrounded by a water insoluble coat containing at least one pore forming additive dispersed throughout said coat. --

At Column 16, line 63, delete "polethylene" and insert therefor -- polyethylene --.

At Column 17, line 23, after "Method" insert -- of --.

At Column 18, line 15, delete "deliver" and insert therefor -- delivery --.

UNITED STATES PATENT AND TRADEMARK OFFICE
CERTIFICATE OF CORRECTION

PATENT NO. : 4,946,686

DATED : August 7, 1990

INVENTOR(S) : Gregory A. McClelland & Gaylen M. Zentner

It is certified that error appears in the above-identified patent and that said Letters Patent is hereby corrected as shown below:

At Column 18, line 16, delete "not" and insert therefor --no--.

Signed and Sealed this

Fourth Day of February, 1992

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,946,686

DATED : August 7, 1990

INVENTOR(S) : G.A. McClelland et al.

It is certified that error appears in the above-identified patent and that said Letters Patent is hereby corrected as shown below:

At Column 4, line 13, after "by" insert -- a --.

At Column 5, line 43, delete "ability".

At Column 13, line 45, delete "invermectin" and insert -- ivermectin --.

Signed and Sealed this

Sixth Day of April, 1993

Attest:

STEPHEN G. KUNIN

*Attesting Officer*     Acting Commissioner of Patents and Trademarks